United States Patent [19]

Gengnagel et al.

[11] 3,947,512

[45] Mar. 30, 1976

[54] PROCESS FOR THE MANUFACTURE OF AROMATIC SULFONIC ACID HALIDES

[75] Inventors: Kurt Gengnagel, Offenbach, Main; Theodor Papenfuhs, Frankfurt am Main; Manfred Zimmermann, Offenbach, Main, all of Germany

[73] Assignee: Hoechst Aktiengesellschaft, Frankfurt am Main, Germany

[22] Filed: Feb. 20, 1974

[21] Appl. No.: 444,260

[30] Foreign Application Priority Data

Feb. 20, 1973   Germany............................ 2308262

[52] U.S. Cl............................................. 260/543 R
[51] Int. Cl.$^2$................................... C07C 143/70
[58] Field of Search ................................. 260/543 R

[56] References Cited
UNITED STATES PATENTS 3,647,873   3/1972   Ziegler et al.................... 260/543 R

FOREIGN PATENTS OR APPLICATIONS 859,461   12/1952   Germany.......................... 260/543 R
64,470    10/1949   Netherlands..................... 260/543 R Primary Examiner—Anton H. Sutto
Attorney, Agent, or Firm—Connolly and Hutz

[57] ABSTRACT

An improved process for the manufacture of aromatic sulfonic acid halides from aromatic diazonium compounds, wherein aromatic diazonium compounds are reacted in a strongly hydrochloric or hydrobromic solution in the presence of copper or copper compounds with an alkali metal hydrogeno-sulfite, which avoids the use of liquid or gaseous sulfur dioxide and of organic solvents according to known processes which makes the process, if carried out on a technical scale, expensive and strongly contaminates the waste water.

2 Claims, No Drawings

PROCESS FOR THE MANUFACTURE OF AROMATIC SULFONIC ACID HALIDES

The present invention relates to an improved process for the manufacture of aromatic sulfonic acid halides from aromatic diazonium compounds.

It is known to prepare aromatic sulfonic acid halides by allowing sulfur dioxide to react on aryl-diazonium halides, especially aryl-diazonium chlorides or bromides, either in the absence of water in an organic solvent or in the presence of water in a strong hydrochloric solution, with addition of hydrosoluble organic acids in the presence of copper or copper compounds (cf. German Pat. No. 859,461).

This process has the disadvantage of being difficult to be carried out on a technical scale, owing to the use of liquid or gaseous sulfur dioxide and of organic solvents, which make the process expensive and strongly contaminate the waste water. In addition, the yields are in many cases unsatisfactory for a technical process.

Now, we have found that aromatic sulfonic acid halides, in particular those of the general formula (1)

$$A - SO_2Cl \qquad (1)$$

in which A represents a phenyl radical which may be substituted by alkyl groups of 1 to 4 carbon atoms, by nitro, trifluoromethyl, carboxy, hydroxy, alkyl-sulfonyl groups of 1 to 4 carbon atoms such as methyl- or ethyl-sulfonyl groups, alkenyl-sulfonyl groups of 1 to 4 carbon atoms such as the vinyl-sulfonyl group, and/or halogen atoms such as fluorine or chlorine, or the naphthyl radical, can be prepared from aromatic diazonium compounds in an essentially easier manner and cheaper and partly also with better yields by reacting aromatic diazonium compounds especially those of amines of the general formula (2)

$$A - NH_2$$

in which A has the meaning given above, in a strongly hydrochloric or hydrobromic solution in the presence of copper or copper compounds with an alkali metal hydrogeno-sulfite.

The process of the invention is carried out by treating a, preferably aqueous, diazonium chloride or diazonium bromide in the presence of copper or copper compounds, advantageously in the absence of organic solvents, with a mixture of alkali metal hydrogeno-sulfite and hydrohalic acid. It is advantageous to use the technically easily accessible sodium bisulfite lye and hydrochloric acid.

The reaction of the diazonium halides takes place in general already at room temperature.

The aryl-sulfonic acid halides formed generally separate during the reaction in liquid or in solid form and are isolated by separation or filtration. The process is suitable for the manufacture of aromatic and aromatic-heterocyclic sulfonic acid halides.

The following Examples illustrate the invention:

EXAMPLE 1

100 Parts by weight of 2-nitro-4-aminobenzoic acid were diazotized with 97.5 parts by weight of 40% sodium nitrite solution and 400 parts by weight of commercial hydrochloric acid at 0°– 5° C and, after a filtration for clarification, introduced dropwise within about 2 hours into a mixture cooled to 3° – 5° C of 1000 parts by weight of commercial hydrochloric acid, 10 parts by weight of crystalline copper sulfate and 175 parts by weight of 40% sodium sulfite lye below the surface. At the same time with the diazo solution, further 175 parts by weight of 40% sodium bisulfite lye were introduced dropwise with the diazo solution below the surface. The diazo compound reacts with strong evolution of nitrogen to the sulfo-chloride. After short stirring, no diazo compound could practically be proved. The sulfo-chloride was filtered off with suction, washed with 2000 parts by volume of water and dried.

121 Parts by weight of 2-nitro-1-benzoic acid-4-sulfonic acid chloride (= 83% of the theory), melting at 190° – 191° C, were obtained.

EXAMPLE 2

200 Parts by weight of 1-amino-2-methyl-4-nitrobenzene were diazotized at 0° – 5° C with 400 parts by weight of 30% hydrochloric acid and 235 parts by weight of 40% sodium nitrite solution. The clarified diazo solution was allowed to run, with slight external cooling, below the surface of a mixture of 1300 parts by weight of 30% hydrochloric acid, 33 parts by weight of crystalline copper sulfate and 330 parts by weight of 40% sodium bisulfite lye, while adding at the same time further 330 parts by weight of 40% sodium bisulfite lye. After about 45 minutes, the sulfonic acid chloride that had separated was filtered off with suction, washed with 2000 parts by volume of cold water and dried. The 2-methyl-4-nitrobenzene-sulfonic acid chloride was obtained in a yield of 85% of the theory and was found to melt at 105° – 106° C.

The sulfonic acid chlorides mentioned below can be prepared in analogous manner.

| Compound | Melting or boiling point | Yield (in % of the theory) |
| --- | --- | --- |
| 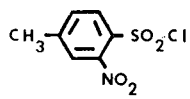 | 96 – 97°C | 83% |
| 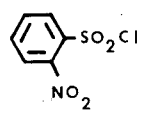 | 65°C | 88% |

-continued

| Compound | Melting or boiling point | Yield (in % of the theory) |
|---|---|---|
| 2-chlorobenzenesulfonyl chloride | 143 – 145°/12mm Hg | 90% |
| 4-chlorobenzenesulfonyl chloride | 53°C | 91% |
| 4-chloro-3-nitro-? benzenesulfonyl chloride (Cl, SO₂Cl, NO₂) | 76°C | 90% |
| 4-chloro-2-trifluoromethyl benzenesulfonyl chloride | 58 – 59°C | 75% |
| CH₂=CH—SO₂—C₆H₄—SO₂Cl | 99 – 100°C | 90% |
| 4-fluorobenzenesulfonyl chloride | 36 – 36°C | 71% |
| 2-hydroxy-5-chlorosulfonyl benzoic acid (OH, COOH, SO₂Cl) | 171°C (decomposition) | 75% |
| 2-chloro-3-nitro benzenesulfonyl chloride (NO₂, Cl, SO₂Cl) | 76 – 78°C | 79% |
| 2,5-substituted (Cl, CF₃, SO₂Cl) | 120 – 125°C/14 mm Hg | 78% |
| HOOC—C₆H₄—SO₂Cl | 232°C | 75% |
| NO₂—C₆H₄—SO₂Cl | 179 – 180°/17 mm Hg | 88% |
| NO₂—C₆H₃(Cl)—SO₂Cl | 76°C | 85% |
| naphthalene-1-sulfonyl chloride | 67°C | 72% |

We claim:
1. A process for the manufacture of aromatic sulfonic acid chlorides of the formula

A — SO$_2$Cl in which A is phenyl or phenyl substituted by a group or groups selected from alkyl of 1 to 4 carbon atoms, nitro, trifluoromethyl, carboxy, hydroxy, alkylsulfonyl of 1 to 4 carbon atoms, alkenylsulfonyl of 1 to 4 carbon atoms or halogen, or is naphthyl, which comprises reacting in an aqueous strongly hydrochloride solution in the absence of an organic solvent and in the presence of copper or copper compounds a diazonium compound of an aromatic amine of the formula

A — NH$_2$ wherein A is defined as above, with an alkali metal hydrogen sulfite.

2. A process as claimed in claim 1, wherein the diazonium compounds are diazonium chlorides or diazonium bromides or their double salts.

* * * * *